(12) United States Patent
Yang et al.

(10) Patent No.: US 7,893,186 B2
(45) Date of Patent: Feb. 22, 2011

(54) PROCESS FOR PREPARING LONG-CHAIN POLYMETHYLENE HALIDE TELOMERS

(75) Inventors: Yu Yang, Eden Prairie, MN (US); George G. I. Moore, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 32 days.

(21) Appl. No.: 12/519,649

(22) PCT Filed: Dec. 27, 2007

(86) PCT No.: PCT/US2007/088906

§ 371 (c)(1),
(2), (4) Date: Jun. 17, 2009

(87) PCT Pub. No.: WO2008/083201

PCT Pub. Date: Jul. 10, 2008

(65) Prior Publication Data

US 2009/0312517 A1    Dec. 17, 2009

Related U.S. Application Data

(60) Provisional application No. 60/882,810, filed on Dec. 29, 2006, provisional application No. 60/882,798, filed on Dec. 29, 2006.

(51) Int. Cl.
*C08G 63/02* (2006.01)
*C08G 64/00* (2006.01)

(52) U.S. Cl. .................. 528/271; 528/272; 528/373; 528/392

(58) Field of Classification Search .......... 528/70, 528/271, 272, 373, 392, 397
See application file for complete search history.

(56) References Cited

U.S. PATENT DOCUMENTS

| | | | |
|---|---|---|---|
| 2,440,800 A | 5/1948 | Hanford et al. |
| 2,440,801 A | 5/1948 | Hanford et al. |
| 2,457,229 A | 12/1948 | Hanford et al. |
| 2,567,011 A | 1/1949 | Diesslin et al. |
| 2,519,983 A | 8/1950 | Simons |
| 2,592,069 A | 4/1952 | Reid |
| 2,642,416 A | 6/1953 | Ahlbrecht et al. |
| 2,662,835 A | 12/1953 | Reid |
| 2,693,458 A | 11/1954 | Olson |
| 2,727,923 A | 12/1955 | Husted |
| 2,732,398 A | 1/1956 | Brice et al. |
| 2,759,019 A | 8/1956 | Brown et al. |
| 2,764,602 A | 9/1956 | Ahlbrecht |
| 2,764,603 A | 9/1956 | Ahlbrecht |
| 2,803,615 A | 8/1957 | Albrecht et al. |
| 2,803,656 A | 8/1957 | Ahlbrecht et al. |
| 2,809,990 A | 10/1957 | Brown et al. |
| 2,846,472 A | 8/1958 | Van Dyke Tiers |
| 2,875,253 A | 2/1959 | Barnhart |
| 2,915,554 A | 12/1959 | Ahlbrecht et al. |
| 3,016,407 A * | 1/1962 | Brace ................. 570/125 |
| 3,050,555 A | 8/1962 | Van Dyke Tiers |
| 3,068,187 A | 12/1962 | Archibald et al. |
| 3,094,547 A | 6/1963 | Heine |
| 3,102,103 A | 8/1963 | Ahlbrecht et al. |
| 3,145,222 A | 8/1964 | Brace |
| 3,171,861 A | 3/1965 | Ahlbrecht |
| 3,341,497 A | 9/1967 | Sherman et al. |
| 3,398,182 A | 8/1968 | Guenthner et al. |
| 3,514,487 A * | 5/1970 | Sweeney et al. ........... 568/684 |
| 3,562,156 A | 2/1971 | Francen |
| 3,573,332 A | 3/1971 | Fenton |
| 3,574,791 A | 4/1971 | Sherman et al. |
| 3,592,866 A | 7/1971 | Magoon et al. |
| 3,641,171 A | 2/1972 | Spooncer |
| 3,787,351 A | 1/1974 | Olson |
| 3,818,074 A | 6/1974 | Ahlbrecht |
| 3,842,019 A | 10/1974 | Kropp |
| 3,896,251 A | 7/1975 | Landucci |

(Continued)

FOREIGN PATENT DOCUMENTS

EP    0 526 976 B1    1/1997

(Continued)

OTHER PUBLICATIONS

*Encyclopedia of Polymer Science and Engineering*, "Telomerization", John Wiley & Sons, Inc., vol. 16, pp. 533-554 (1989).

(Continued)

*Primary Examiner*—Terressa M Boykin
(74) *Attorney, Agent, or Firm*—Lucy C. Weiss

(57) ABSTRACT

A process comprises combining in a batchwise, semi-continuous, or continuous manner, or a combination thereof, in the presence of at least one free radical initiator, and at a temperature sufficient to cause the initiator to fragment to form free radicals, (a) at least one telogen selected from (1) fluoroalkyl halides that comprise at least one halomethylene moiety (—CHX—) and, optionally, at least one non-fluorine heteroatom, and (2) perfluoroalkyl halides that comprise at least one halofluoromethylene moiety (—CFX—) and at least one non-halogen heteroatom, the halides being selected from iodides and bromides; and (b) ethylene; the telogen and the ethylene being combined in total amounts such that the number of moles of ethylene per mole of telogen is at least about 4.

20 Claims, No Drawings

U.S. PATENT DOCUMENTS

| | | | |
|---|---|---|---|
| 3,916,053 | A | 10/1975 | Sherman et al. |
| 4,024,178 | A | 5/1977 | Landucci |
| 4,043,923 | A | 8/1977 | Loudas |
| 4,264,484 | A | 4/1981 | Patel |
| 4,359,096 | A | 11/1982 | Berger |
| 4,401,780 | A | 8/1983 | Steel |
| 4,484,990 | A | 11/1984 | Bultman et al. |
| 4,529,658 | A | 7/1985 | Schwartz et al. |
| 4,540,497 | A | 9/1985 | Chang et al. |
| 4,606,737 | A | 8/1986 | Stern |
| 4,668,406 | A | 5/1987 | Chang |
| 5,025,052 | A | 6/1991 | Crater et al. |
| 5,207,996 | A | 5/1993 | Sierakowski et al. |
| 5,216,097 | A | 6/1993 | Allewaert et al. |
| 5,240,574 | A | 8/1993 | Fuss et al. |
| 5,244,951 | A | 9/1993 | Gardiner |
| 5,271,806 | A | 12/1993 | Deutsch et al. |
| 5,276,175 | A | 1/1994 | Dams et al. |
| 5,380,778 | A | 1/1995 | Buckanin |
| 5,431,833 | A | 7/1995 | Kondo et al. |
| 5,451,622 | A | 9/1995 | Boardman et al. |
| 5,468,353 | A | 11/1995 | Anich et al. |
| 5,612,431 | A | 3/1997 | Waddell et al. |
| 5,641,844 | A | 6/1997 | Thompson et al. |
| 5,725,789 | A | 3/1998 | Huber et al. |
| 5,744,201 | A | 4/1998 | Chang et al. |
| 6,048,952 | A | 4/2000 | Behr et al. |
| 6,326,447 | B1 | 12/2001 | Fitzgerald |
| 6,365,769 | B1 | 4/2002 | Behr et al. |
| 6,824,882 | B2 | 11/2004 | Boardman et al. |
| 2010/0093925 | A1 | 4/2010 | Moore et al. |
| 2010/0234521 | A1 | 9/2010 | Flynn et al. |

FOREIGN PATENT DOCUMENTS

| | | | |
|---|---|---|---|
| GB | 1 415 245 | | 11/1975 |
| GB | 1415245 | * | 11/1975 |

OTHER PUBLICATIONS

Boyer et al., "Reverse Iodine Transfer Polymerization (RITP) of Methyl Methacrylate", Macromolecules, pp. 4044-4053, vol. 39 (2006).

Boyer et al., "Iodine Transfer Polymerization (ITP) of Vinylidene Fluoride (VDF). Influence of the Defect of VDF Chaining on the Control of ITP", *Macromolecules*, pp. 10353-10362, vol. 38 (2005).

Brace, "Radical Addition of Iodoperiluoroalkanes to Vinyl and Allyl Monomers", Contribution No. 313, Research Division, Organic Chemicals Department, E.I. du Pont de Nemours and Company, Wilmington, Delaware, *Journal of Organic Chemistry*, pp. 3033-3038, vol. 27 (Sep. 1962).

U.S. Appl. No. 12/519,573; filed on Dec. 27, 2007; Titled: Long-Chain Polymethylene Halide Telomers; published as US 2010/0093925 (see above).

U.S. Appl. No. 12/377,873; filed on Aug. 17, 2007; Titled: Side Chain Fluorochemicals with Crystallizable Spacer Groups; published as US 2010/0234521 (see above).

International Search Report for International Application No. PCT/US2007/088906.

\* cited by examiner

PROCESS FOR PREPARING LONG-CHAIN POLYMETHYLENE HALIDE TELOMERS

STATEMENT OF PRIORITY

This application claims the priority of U.S. Provisional Application Nos. 60/882,810 and 60/882,798 filed Dec. 29, 2006, the contents of which are hereby incorporated by reference.

FIELD

This invention relates to processes for preparing telomers of ethylene and fluoroalkyl or perfluoroalkyl halides.

BACKGROUND

Fluorinated polymers typically comprise repeating units, each unit including a backbone portion attached to a fluoroalkyl side chain. The fluoroalkyl side chain typically includes a hydrocarbon spacer group and a terminal perfluoroalkyl tail. The stable and inert perfluoroalkyl tail is hydrophobic and oleophobic.

Such fluorinated polymers can be mixed with an inert carrier or dissolved in a solvent and applied to a hydrophilic material (for example, paper, cloth, metals, glass, or ceramic) to impart water and oil repellency to the material. The perfluoroalkyl tail portions of the polymer can organize or align at the solid/air interface of the material to create a low energy surface.

Conventional fluoroalkyl side chains generally have the formula $C_nF_{2n+1}(CH_2)_m$— where n typically ranges from 6 to 12, and m typically ranges from 1 to 11. Adjustment of the number of methylene moieties (—$CH_2$—) in the spacer group, as well as the number of carbon atoms in the $C_nF_{2n+1}$ perfluoroalkyl tail, can result in the organization or alignment of the side chains of the polymers and in the formation of crystalline-like regions when the polymer is applied to a substrate material. It has been postulated that an increase in the number of methylene moieties in the spacer group can compensate for the decrease in the value of n that is now viewed as desirable from an environmental residue perspective.

In synthesizing conventional fluorinated polymers, however, the perfluoroalkyl chain length generally has been the only part of the side chain that has been varied to enhance the formation of crystalline regions (and the accompanying ability to impart low surface energy characteristics). This may have been due to a scarcity of industrially useful methods for preparing side chains of varying polymethylene content.

Compounds comprising polymethylene moieties have been prepared by different synthetic techniques, but each has its own advantages and disadvantages. One such method has been the telomerization of ethylene using various telogens.

Telomerization has been defined as the process of reacting, under polymerization conditions, a molecule YZ (termed a "telogen") with more than one unit of a polymerizable compound having ethylenic unsaturation (termed a "taxogen") to form products called "telomers" having the formula $Y(A)_nZ$, wherein $(A)_n$ is a divalent radical formed by chemical union, with the formation of new carbon bonds, of n molecules of the taxogen (the unit A being termed a "taxomon," n being any integer greater than one, and Y and Z being fragments of the telogen attached to the terminal taxomons). Telomerization is distinct from interpolymerization (more commonly referred to as copolymerization), in that in telomerization only one molecule of telogen is incorporated into each resulting telomer molecule, and the average molecular weight of the telomer product is, in general, considerably lower than that of an interpolymer formed under comparable conditions.

Ethylene telomerization produces a mixture or distribution of telomers having varying numbers of methylene moieties. For the telogens selected and the conditions utilized, however, ethylene telomerizations have typically resulted in telomers of only limited chain length. Industrial use of fluoroalkyl or perfluoroalkyl halides, in particular, has typically focused on the incorporation of only one molecule of ethylene (n=1).

SUMMARY

Thus, we recognize that there is a need for processes for preparing sidechain precursor compounds having varying numbers of methylene moieties. In particular, there is a need for processes for preparing sidechain precursor compounds having more than the 1-11 methylene moieties found in sidechains made by conventional synthetic techniques (for repellency applications, preferably, in combination with a terminal fluorinated group). Such processes will preferably be simple and cost-effective and thereby amenable to industrial use.

Briefly, in one aspect, this invention provides such a process, which comprises combining in a batchwise, semi-continuous, or continuous manner, or a combination thereof, in the presence of at least one free radical initiator, and at a temperature sufficient to cause the initiator to fragment to form free radicals, (a) at least one telogen selected from (1) fluoroalkyl halides that comprise at least one halomethylene moiety (—CHX—) and, optionally, at least one non-fluorine heteroatom, and (2) perfluoroalkyl halides that comprise at least one halofluoromethylene moiety (—CFX—) and at least one non-halogen heteroatom, the halides being selected from iodides and bromides; and (b) ethylene; the telogen and the ethylene being combined in total amounts such that the number of moles of ethylene per mole of telogen is at least about 4 (that is, at least about 2 times the desired average number of moles of ethylene taxomons to be incorporated in a resulting telomer product). Preferably, the telogen is selected from the above-described fluoroalkyl halides and/or the molar ratio of ethylene to telogen is at least about 8 (more preferably, at least about 10, although the preferred molar ratio can vary somewhat, depending upon the desired telomer chain length relative to the number of methylene moieties in the starting telogen).

It has been discovered that by selecting certain fluoroalkyl halide or perfluoroalkyl halide telogens and certain reaction conditions, including the use of certain reactant ratios, ethylene can be telomerized according to the process of the invention to provide relatively long-chain telomers. In addition, the process surprisingly appears to exhibit the characteristics of a living polymerization, in that the resulting telomers can serve as the starting materials for further telomerization by introducing additional initiator and ethylene under the reaction conditions.

Telomers produced by the process of the invention preferably contain more than 10 methylene moieties and, for example, up to as many as 30 methylene moieties or more (for example, up to as many as 50), depending upon, for example, the selected reactants, ratios of reactants, and reaction conditions. The telomers can be produced in the form of a distribution (that is, a mixture of varying chain-length compounds, which differ in the number of incorporated ethylene units), and, unlike conventional polymethylene telomer distributions that have a number average ratio of internal methylene moieties (for example, of the ethylene taxomons derived from the ethylene taxogen) to terminal halomethyl groups (for example, comprising the halogen atom of the selected telogen) of no more than about 7, the distributions can exhibit number average ratios of at least about 15 (preferably, at least about 20). The number average molecular weights of the telomer distributions can be determined by nuclear magnetic resonance spectroscopy (NMR), gas chromatography (GC), or other suitable techniques (preferably, by NMR).

Since at least some embodiments of the process provide telomer distributions that can be used as fluoroalkyl sidechain precursors, such embodiments can meet the need for industrially useful processes for preparing sidechain precursor compounds having varying numbers of methylene moieties and, in at least preferred embodiments, more than the 1-11 methylene moieties found in conventional sidechains. Such embodiments provide an economical source of crystallizable polymethylene, as the process of the invention does not require multiple reaction steps.

In addition, the telomer products of such embodiments can comprise a relatively short perfluoroalkyl tail portion that can be lower in cost (and easier to prepare and process) than longer perfluoroalkyl tail portions and that is also believed to provide for relatively low bio-accumulation. Such products therefore can be environmentally friendly, yet still can be effective in imparting fluorochemical repellency characteristics (for example, water and oil repellency), apparently due to the above-mentioned compensation effect of the lengthy polymethylene segment (which enables the use of the shorter perfluoroalkyl tail portion).

DETAILED DESCRIPTION

Definitions

As used in this patent application:

"catenated heteroatom" means an atom other than carbon (for example, oxygen, nitrogen, or sulfur) that is bonded to carbon atoms in a carbon chain so as to form a carbon-heteroatom-carbon chain;

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Telogens

Telogens that can be suitable for use in the process of the invention include fluoroalkyl halides that comprise at least one halomethylene moiety (—CHX—) and, optionally, at least one non-fluorine heteroatom; and perfluoroalkyl halides that comprise at least one halofluoromethylene moiety (—CFX—) and at least one non-halogen heteroatom. The halides can be iodides or bromides or a mixture thereof. Iodides can be preferred due to the availability of a wide variety of iodide compounds, and bromides, although previously viewed as less reactive and therefore less available, can be preferred due to their lower cost. Preferably, the heteroatoms are selected from iodine, bromine, nitrogen, oxygen, and sulfur. More preferably, the heteroatoms are present as a single iodine or bromine atom, as a catenated oxygen, nitrogen, or sulfur atom (for example, an ether oxygen moiety, the in-chain oxygen atom of an ester moiety, or the in-chain sulfur atom of a sulfonyl moiety), or as part of a terminal functional group (for example, carboxyl, cyano, sulfonato, acyloxy (or alkyl carboxylate), sulfonamido, and carboxamido moieties, and the like, and combinations thereof). The fluoroalkyl and perfluoroalkyl groups can optionally comprise one or more cyclic moieties. Preferably, the telogens are saturated.

One class of suitable fluoroalkyl halides is that which can be represented by the following general formula:

$$R'CH(R)X \qquad (I)$$

wherein R' is fluorine or a fluoroalkyl or perfluoroalkyl group of 1 to about 25 carbon atoms (preferably, 1 to about 10 carbon atoms; more preferably, 1 to about 6 carbon atoms; most preferably, 1 to about 4 carbon atoms) that optionally comprises at least one non-fluorine heteroatom and/or at least one alicyclic moiety; R is hydrogen, fluorine, or a fluoroalkyl or perfluoroalkyl group of 1 to about 25 carbon atoms (preferably, 1 to about 10 carbon atoms; more preferably, 1 to about 6 carbon atoms; most preferably, 1 to about 4 carbon atoms) that optionally comprises at least one non-fluorine heteroatom and/or at least one alicyclic moiety; and X is iodine or bromine; with the proviso that R' and R can be bonded together to form an alicyclic ring having from 5 to about 7 ring carbon atoms. Preferably, the heteroatom is selected from iodine, bromine, nitrogen, oxygen, and sulfur (more preferably, nitrogen, oxygen, and sulfur; even more preferably, nitrogen or oxygen; most preferably, oxygen).

R' is preferably a fluoroalkyl or perfluoroalkyl group that optionally comprises at least one non-fluorine heteroatom. R is preferably hydrogen or perfluoroalkyl (more preferably, hydrogen, perfluoroisopropyl, or perfluoromethyl; most preferably, hydrogen or perfluoromethyl). R' and R preferably do not comprise an alicyclic moiety.

Representative examples of suitable fluoroalkyl halide telogens include $CF_3CH_2I$, $CF_3OCH(CF_3)I$, $CF_3CH(CF_3)Br$, $H(CF_2)_6CH_2I$, $CF_3C_3H_6I$, $C_2F_5C_2H_4I$, $CF_3CH_2Br$, $C_2F_5C_2H_4Br$, $(CF_3)_2CFCH_2I$, $C_4F_9C_2H_4I$, $C_4F_9C_3H_6I$, $C_4F_9C_4H_8Br$, $C_6F_{13}CH_2Br$, $CF_3OC_2H_4I$, $C_4F_9OCH_2Br$, $C_3F_7CH_2OC_2H_4I$, $C_4F_9SO_2N(CH_3)C_2H_4I$, $C_2F_5OC_2F_4C_2H_4I$, $CF_3OC_2F_4CH_2Br$, $(CF_3)_2CHOC_2H_4I$, $C_2F_5SO_2N(CH_3)CH_2C(O)CH_2I$, $(CF_3)_2NC_2F_4CH_2I$, $C_3F_7N(CF_3)CF_2C_2H_4Br$, $FSO_2C_3F_6C_2H_4I$, $(CF_3)_2NCH_2I$, $(CF_3)_2NCF_2CH_2I$, $CH_3OC(O)C_4F_8CH_2I$, $(CF_3)_2CHI$, and the like, and mixtures thereof. Also useful are telogen mixtures (for example, $C_4F_9(CH_2)_nI$, where n is a number average value (that is, an average value that is calculated from the number average molecular weight of the mixture) of 1 to about 17) that can be obtained, for example, as a distribution from a prior, "partial" telomerization and recycled for further telomerization.

Preferred fluoroalkyl halide telogens include $CH_3OC(O)C_4F_8CH_2I$, $C_2F_5C_2H_4I$, $(CF_3)_2CFCH_2I$, $C_4F_9C_2H_4I$, $C_2F_5SO_2N(CH_3)CH_2C(O)CH_2I$, $C_4F_9SO_2N(CH_3)C_2H_4I$, $CF_3OC_2F_4CH_2Br$, $(CF_3)_2CHOC_2H_4I$, $(CF_3)_2CHI$, and mixtures thereof. More preferred are $(CF_3)_2CFCH_2I$, $C_4F_9C_2H_4I$, $C_4F_9SO_2N(CH_3)C_2H_4I$, $CF_3OC_2F_4CH_2Br$, $(CF_3)_2CHOC_2H_4I$, $(CF_3)_2CHI$, and mixtures thereof, with $(CF_3)_2CFCH_2I$, $C_4F_9C_2H_4I$, $C_4F_9SO_2N(CH_3)C_2H_4I$, $(CF_3)_2CHI$, and mixtures thereof being most preferred.

One class of suitable perfluoroalkyl halides is that which can be represented by the following general formula:

$$R'''CF(R'')X \qquad (II)$$

wherein R''' is a perfluoroalkyl group of 1 to about 25 carbon atoms (preferably, 1 to about 10 carbon atoms; more preferably, 1 to about 6 carbon atoms; most preferably, 1 to about 4 carbon atoms) that optionally comprises at least one alicyclic moiety and/or at least one non-fluorine halogen atom (preferably, iodine or bromine; when present, preferably only one such halogen atom); R'' is fluorine or a perfluoroalkyl group of 1 to about 25 carbon atoms (preferably, 1 to about 10 carbon atoms; more preferably, 1 to about 6 carbon atoms; most preferably, 1 to about 4 carbon atoms); and X is iodine or bromine; with the proviso that at least one of R''' and R'' comprises at least one non-halogen heteroatom, and with the further proviso that R''' and R'' can be bonded together to form an alicyclic ring having from 5 to about 7 ring carbon atoms. Preferably, the heteroatom is selected from nitrogen, oxygen, and sulfur (more preferably, nitrogen or oxygen; most preferably, oxygen).

R''' preferably is a perfluoroalkyl group that comprises at least one non-halogen heteroatom. R'' is preferably fluorine or perfluoroalkyl (more preferably, fluorine, perfluoroisopropyl, or perfluoromethyl; most preferably, fluorine or perfluoromethyl). R''' and R'' preferably do not comprise an alicyclic moiety or a non-fluorine halogen atom.

Representative examples of suitable perfluoroalkyl halide telogens include $FSO_2C_2F_4OC_2F_4I$, $FSO_2C_3F_6Br$, $CF_3OC_2F_4I$, $CF_3OCF(CF_3)I$, $(CF_3)_2CFOC_2F_4I$, $C_3F_7O(i-C_3F_6O)_pCF(CF_3)I$ (where p is an integer of 0 to 7), $C_3F_7O(i-C_3F_6O)_pCF(CF_3)Br$ (where p is an integer of 0 to 7), $C_3F_7O(n-C_3F_6O)_pCF(CF_3)I$ (where p is an integer of 0 to 7), $FOC(O)C_5F_{10}I$, and the like, and mixtures thereof. Preferred perfluoroalkyl halide telogens include $FSO_2C_2F_4OC_2F_4I$, $FSO_2C_3F_6Br$, $CF_3OC_2F_4I$, $FOC(O)C_5F_{10}I$, $(CF_3)_2CFOC_2F_4I$, $C_3F_7O(i-C_3F_6O)_pCF(CF_3)I$ (where p is an integer of 5 to 7), and mixtures thereof. More preferred are $FSO_2C_2F_4OC_2F_4I$, $FOC(O)C_5F_{10}I$, $(CF_3)_2CFOC_2F_4I$, $C_3F_7O(i-C_3F_6O)_pCF(CF_3)I$ (where p is an integer of 5 to 7), and mixtures thereof, with $FSO_2C_2F_4OC_2F_4I$ and $C_3F_7O(i-C_3F_6O)_pCF(CF_3)I$ (where p is an integer of 5 to 7), and mixtures thereof being most preferred.

Preferred telogens include those that comprise a sulfonamido moiety, a perfluoropolyether moiety, or a relatively low carbon number (fewer than about 6 carbon atoms) perfluoroalkyl moiety, as such telogens tend to provide telomer distributions that can exhibit relatively low bio-accumulation characteristics. In general, preferences can be based upon economic factors (for example, cost, availability, or ease of handling) or upon performance factors (for example, of the telogen or the resulting telomer distribution).

The heteroatoms can be present in the fluoroalkyl halide and perfluoroalkyl halide telogens in the form of functional groups (for example, alkoxy, alkanoyloxy, alkyloxyacyl, cyano, sulfonyl, and like groups having no active hydrogen atoms). Such functional groups can be useful as strong acids for catalysts (for example, —COOH or —SO$_3$H) or anionic surfactants or as reactive intermediates (for example, as in polymer formation). The additional non-fluorine halogen atoms, when in the form of iodine or bromine bonded to carbon, can provide additional reactive sites for insertion of ethylene. Preferred telogens include the fluoroalkyl halides and mixtures thereof.

The above-described telogens can be prepared by known methods. For example, the fluoroalkyl halides can be prepared by displacement of a leaving group (on the fluoroalkyl moiety) by bromide or iodide, and the perfluoroalkyl halides can be prepared by the reaction of a perfluoroolefin (for example, tetrafluoroethylene or hexafluoropropylene) with $IF_5$ or by decarbonylation of perfluoroacyl halides. Some of the telogens (for example, $FSO_2C_2F_4OC_2F_4I$ and $I(CF_2)_4I$ are commercially available.

Telomer Preparation Process

The telomerization process can be conducted neat or, optionally, in the presence of a reaction diluent that is liquid at the selected reaction temperature and pressure, that is capable of dissolving or dispersing the reactants and initiator(s), and that is inert to the reactants, the initiator(s), and the resulting telomer products. Suitable diluents include water (for suspension or emulsion techniques), supercritical carbon dioxide, perfluorocarbons, hydrofluoroethers (HFEs), hexafluorobenzene, trifluorotoluene, hexafluoroxylene, alkanes, benzene, and the like, and mixtures thereof). Preferred diluents include fluorine-containing diluents, due to their generally low reactivity toward free radical intermediates. If desired, a portion of the telomer product can serve as at least a portion of the diluent (with less or no added diluent being required). Amounts of diluent up to about 30 times the weight of telogen generally can be employed.

The telomerization process can be conducted by any of a variety of procedures. If desired, ethylene, telogen(s), free radical initiator(s), and diluent(s) can be charged (in essentially any order and manner of combination) to an autoclave or similar pressure reactor (made, for example, of stainless steel, optionally with a glass liner, and optionally equipped with agitation means). The process can be carried out in a batchwise manner. Alternatively, the process can be carried out in a semi-continuous or continuous manner (with continuous introduction of reactants and/or continuous removal of product) by, for example, using a tubular reactor. If desired, one reaction component can be added to the other reaction components in increments (for example, by adding ethylene to a solution of telogen and free radical initiator). The various different manners of carrying out the process can be combined, if desired.

The telomerization process can be preferably and most efficiently conducted at elevated temperature and pressure. In general, temperatures varying from about 0° C. to about 250° C. can be utilized (depending, for example, upon the particular free radical initiator that is selected), with temperatures from about 75° C. to about 125° C. often being preferred. In general, a preferred temperature can reflect a selected balance between lower reactivity at lower temperatures and an increased tendency toward side reactions at higher temperatures.

Reaction pressures from about 10 atmospheres to about 350 atmospheres (preferably, from about 50 atmospheres to about 350 atmospheres; more preferably, from about 100 atmospheres to about 350 atmospheres) generally can be satisfactory. If desired, the telomerization process can be conducted in an inert reaction environment, so that the presence of reactive materials such as oxygen can be avoided. Preferably, the reaction conditions can be substantially oxygen-free.

In general, molar ratios of the total amount of ethylene to the total amount of telogen ("total molar ratios") of from about 4:1 to about 400:1 can be satisfactory, with total molar ratios from about 8:1 to about 300:1 being preferred (more preferably, about 10:1 to about 200:1; even more preferably, about 50:1 to about 150:1; most preferably, about 70:1 to about 125:1). The selection of total molar ratio will depend upon the desired methylene moiety content of the telomer product relative to the methylene moiety content of the starting telogen and will generally be at least about twice the number of moles of ethylene desired to be incorporated through the telomerization process per mole of telogen. (In general, at lower ratios, the rate and degree of telomerization can be lower than desired.)

Although such total (or overall) molar ratios generally can be maintained throughout the process, some deviation (for example, for less than about 25 percent of the total reaction time) can be tolerated and is to be expected as ethylene is consumed. The instantaneous molar ratio of ethylene to telogen thus can vary over a wide range, although it generally can be useful to employ a stoichiometric excess of ethylene (relative to the desired telomer product).

Free radical-generating initiators are well-known. Useful thermal free radical initiators include, but are not limited to, the following: (1) azo compounds such as, for example, 2,2'-azo-bis(isobutyronitrile), 2,2'-azo-bis(isovaleronitrile), dimethyl 2,2'-azo-bis(isobutyrate), azo-bis(diphenyl methane), and 4,4'-azo-bis(4-cyanopentanoic acid); (2) peroxides such as, for example, hydrogen peroxide, benzoyl peroxide, cumyl peroxide, tert-butyl peroxide, cyclohexanone peroxide, glutaric acid peroxide, lauroyl peroxide, and methyl ethyl ketone peroxide; (3) hydroperoxides such as, for example, tert-butyl hydroperoxide and cumene hydroperoxide; (4) peracids such as, for example, peracetic acid, perbenzoic acid, potassium persulfate, and ammonium persulfate; (5) peresters such as, for example, tert-butyl perbenzoate and diisopropyl percarbonate; (6) thermal redox initiators; and the like; and mixtures thereof.

Preferred free radical initiators include azo compounds, peroxides, peresters, and mixtures thereof. More preferred are free radical initiators selected from 2,2'-azo-bis(isobutyronitrile), 2,2'-azo-bis(isovaleronitrile), benzoyl peroxide, tert-butyl peroxide, tert-butyl perbenzoate, and mixtures thereof (most preferably, those selected from 2,2'-azo-bis(isobutyronitrile), tert-butyl perbenzoate, and mixtures thereof). The free radical initiator can be used in a catalytically effective amount (for example, up to about 5 weight percent (preferably, about 1 to about 5 weight percent; more preferably, about 2 weight percent), based upon the total weight of telogen). Initiator can be added all at once or in increments, as desired.

The telomer product distribution from the reactor can be used as recovered or, optionally, can be separated into a telomer fraction having a higher selected numerical range of carbon atoms and a telomer fraction having a lower selected numerical range of carbon atoms by using, for example, fractional distillation, selective extraction, adsorption, and the like, and combinations thereof. The lower telomer fraction, along with any unreacted telogen, can be recycled to the reactor for further reaction with ethylene to produce additional higher molecular weight (longer chain) telomer products. Generally, however, relatively long-chain telomers can be produced (by proper selection of the ratio of reactants and the reaction temperature) without the need for such separation and recycling.

Product Composition

The process of the invention can provide a composition that comprises a distribution of fluoroalkyl halide telomers that comprise at least one polymethylene segment ($-(CH_2)_n-$) and at least one halomethyl group ($-CXH_2$). The telomers optionally comprise at least one non-fluorine heteroatom, and the halogen is selected from iodine and bromine. The distribution preferably exhibits a number average ratio of the methylene moieties of the polymethylene segment to the halomethyl groups of at least about 15, as determined by nuclear magnetic resonance spectroscopy (NMR), gas chromatography (GC), or other suitable techniques (preferably, by NMR).

More preferably, the number average ratio is at least about 20 (in view of, for example, preferred crystallization characteristics).

A preferred class of product telomer compositions is that which can be represented by the following general formula:

$$R'CH(R)-(CH_2)_n-X \quad\quad (III)$$

wherein R', R, and X are as defined above for Formula I, and n is a number average value (that is, an average value that is calculated from the number average molecular weight of the composition) of at least about 15 (preferably, at least about 20).

Another preferred class of product telomer compositions is that which can be represented by the following general formula:

$$R'''CF(R'')-(CH_2)_n-X \quad\quad (IV)$$

wherein R''', R'', and X are as defined above for Formula II, and n is a number average value of at least about 15 (preferably, at least about 20).

Representative examples of such telomer distributions include $CF_3(CH_2)_nI$, $CF_3CF_2(CH_2)_nI$, $(CF_3)_2NCF_2(CH_2)_nI$, $CF_3C_2F_4(CH_2)_nI$, $C_3F_7O(C_3F_6O)_5CF(CF_3)(CH_2)_nI$, $C_4F_9SO_2N(CH_3)(CH_2)_nI$, $FSO_2C_2F_4OC_2F_4(CH_2)_nI$, $CH_3OC(O)CF_2(CH_2)_nI$, $FOC(O)CF_2(CH_2)_nI$, $(CF_3)_2CF(CH_2)_nI$, $(CF_3)_2N(CH_2)_nI$, $(CF_3)_2CHO(CH_2)_nI$, $SF_5CF_2(CH_2)_nI$, $CF_3OC_2F_4(CH_2)_nBr$, $(CF_3)_2CH(CH_2)_nI$, $(CF_3)_3C(CH_2)_nBr$, $C_4F_9SO_2N(CH_3)CH_2C(O)(CH_2)_nI$, where n is a number average value of at least about 15 (for example, 18, 20, 25, 26, 45, and the like), and the like, and mixtures thereof. Telomers having odd numbers of methylene moieties can be obtained by using telogens having an odd number of methylene moieties, which can be advantageous in varying the physical property characteristics (for example, melting point) of the resulting telomers.

Preferred telomer distributions include $CF_3CF_2(CH_2)_nI$, $(CF_3)_2CH(CH_2)_nI$, $C_3F_7O(C_3F_6O)_5CF(CF_3)(CH_2)_nI$, $C_4F_9SO_2N(CH_3)(CH_2)_nI$, $(CF_3)_2CF(CH_2)_nI$, $CF_3OC_2F_4(CH_2)_nBr$, $CH_3OC(O)CF_2(CH_2)_nI$, $FSO_2C_2F_4OC_2F_4(CH_2)_nI$, $(CF_3)_2NCF_2(CH_2)_nI$, $(CF_3)_2CHO(CH_2)_nI$, where n is a number average value of at least about 15 (for example, 18, 20, 25, 26, and 45), and mixtures thereof, with $(CF_3)_2CH(CH_2)_nI$, $C_3F_7O(C_3F_6O)_5CF(CF_3)(CH_2)_nI$, $C_4F_9SO_2N(CH_3)(CH_2)_nI$, $(CF_3)_2CF(CH_2)_nI$, $CF_3OC_2F_4(CH_2)_nBr$, where n is a number average value of at least about 15 (for example, 18, 20, 25, 26, and 45), and mixtures thereof being more preferred.

The preferred telomer compositions prepared by the process of the invention can comprise a mixture of such telomers that can be, for example, a relatively even or flat distribution of about 5 to about 10 different telomers, as indicated by gas chromatography.

The preferred fluoroalkyl halide telomer compositions can be used as fluoroalkyl sidechain precursors in fluorinated polymer preparation. The compositions produced by the process of the invention are reactive chemicals and can be converted into functional derivatives by one or more steps. For example, the terminal halide can be converted by nucleophilic displacement or elimination reactions or by free radical addition to other functional groups such as hydroxyl, amino, mercapto, sulfonato, carboxyl, and vinyl groups, and combinations thereof.

Thus, in a preferred embodiment of the process of the invention, the polymethylene halide telomers (the above-described preferred telomer compositions, as well as those having a smaller number average value of n) resulting from the process can be further converted to the corresponding polymethylene alcohols. For such conversion, the process preferably further comprises (a) combining at least one polymethylene halide telomer with at least one metal carboxylate (preferably, sodium acetate); and (b) subjecting the resulting polymethylene carboxylate to alkanolysis (preferably, methanolysis or ethanolysis); wherein the combining and the subjecting are carried out under substantially anhydrous conditions.

Polymerizable functionalities such as acrylate, methacrylate, and urethane groups can also be achieved and used to produce fluoropolymers. The various functional derivatives can be useful in improving or imparting properties to solutions and substrates such as wetting, penetration, spreading, leveling, foaming, foam stabilization, flow properties, emulsification, dispersability, and oil, water, and soil repellency.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc., in the examples and the rest of the specification are by weight, unless noted otherwise. Solvents and other reagents used were obtained from Aldrich Chemical Company, St. Louis, Mo., unless otherwise noted.

Test Methods

Nuclear Magnetic Resonance (NMR)

$^1$H and $^{19}$F NMR spectra were run on a Varian UNITYplus 400 Fourier transform NMR spectrometer (available from Varian NMR Instruments, Palo Alto, Calif.).

Gas Chromatography/Mass Spectroscopy (GCMS)

GCMS samples were run on, for example, a Finnigan TSQ7000 mass spectrometer (available from Thermo Electron Corporation, Waltham, Mass.).

Gas Chromatography (GC)

GC samples were run on a Hewlett Packard 6890 Series Gas Chromatograph, obtainable from Agilent Technologies, Palo Alto, Calif.

Table of Abbreviations

| Abbreviation or Trade Designation | Description |
|---|---|
| b.p. | Boiling point, measured at ambient pressure unless otherwise specified |
| m.p. | Melting point, measured at ambient pressure unless otherwise specified |
| Wt. or wt. | Weight, measured in grams or in percent (%) as specified |
| g or g. | Gram or grams |
| $M_n$ | Number average molecular weight |

Materials

Ethylene was obtained from Oxygen Service Company, St. Paul, Minn.

t-Butyl benzoylperoxide was obtained from Sigma-Aldrich Chemical Company, St. Louis, Mo.

n-$C_4F_9I$ was obtained from TCI America, Portland, Oreg., and is available from Sigma-Aldrich Chemical Company, St. Louis, Mo.

$C_4F_9SO_2F$ was obtained from 3M Company, St. Paul, Minn.

$C_6F_{13}I$ is available from Sigma-Aldrich Chemical Company, St. Louis, Mo.

$(CF_3)_2CFCH_2CH_2I$ can be prepared by adding $(CF_2)_2CFI$ to ethylene at 60° C. with 2,2'-azo-bis(isobutyronitrile) (AIBN), using methods described in U.S. Pat. No. 3,145,222 (Brace).

$CF_3CF_2CH_2I$ can be prepared by reaction of $C_2F_5CH_2OSO_2C_6H_4$-4-$CH_3$ (available from Synquest Labs, Inc. Alachua, Fla.) with NaI, as described below for $CF_3(CF_2)_3SO_2N(Me)CH_2CH_2I$.

$CF_3(CF_2)_3SO_2N(Me)CH_2CH_2I$ was made as follows: $CF_3(CF_2)_3SO_2N(Me)CH_2CH_2OH$ was reacted with an excess of thionyl chloride in methylene chloride at 25-45° C. to give $CF_3(CF_2)_3SO_2N(Me)CH_2CH_2Cl$, which (7.1 g) was mixed with a solution of 6.0 g NaI in acetone. The resulting solution was stirred at reflux, and the conversion to $CF_3(CF_2)_3SO_2N(Me)CH_2CH_2I$ was followed by GC. At 24 hours, conversion was 14 percent, and 6.0 g more NaI was added; at 3 days, conversion was 46 percent; at 6 days, conversion was 72 percent, and 6.0 g NaI was added; at 13 days, 96 percent conversion was achieved. The resulting product was precipitated with water and recrystallized from hexane to provide 6.2 g white plates with a m.p. of 80-82° C.

$FO_2S(CF_2)_2O(CF_2)_2I$ was obtained from Sigma-Aldrich Chemical Company, St. Louis, Mo.

$C_3F_6O(isoC_3F_3O)_5CF(CF_3)$ can be prepared essentially as described by Chen et. al. in J Fluorine Chem. 65, 59 (1993).

$I(CF_2)_4I$ was obtained from Sigma-Aldrich Chemical Company, St. Louis, Mo.

$CF_3(CF_2)_7Br$ was obtained from 3M Company, St. Paul, Minn., and is available from Sigma-Aldrich Chemical Company, St. Louis, Mo.

Sodium acetate was obtained from Sigma-Aldrich Chemical Company, St. Louis, Mo.

Dimethylsulfoxide (DMSO) was obtained from Alfa Aesar, Ward Hill, Mass.

Tetrahydrofuran (THF) was obtained from EMD Chemicals, Inc., Gibbstown, N.J.

p-Toluenesulfonic acid was obtained from J. T. Baker, Phillipsburg, N.J.

$NaHCO_3$ was obtained from EMD Chemicals, Inc., Gibbstown, N.J.

Example 1

Telomerization of Ethylene Using $(CF_3)_2CFCH_2CH_2I$

A 43 mL stainless steel autoclave was charged with 8 g of $(CF_3)_2CFCH_2CH_2I$ and 0.196 g of t-butyl benzoylperoxide. After the autoclave was cooled in a dry ice bath and degassed using a vacuum pump, 16.2 g of ethylene was introduced. The autoclave was shaken and slowly heated to 100° C. and held at 100° C. overnight. The autoclave was then cooled to room temperature, any remaining gases were released, and 9.9 g of a wax-like product was recovered.

The wax-like product, comprising a mixture of telomers having the formula $[(CF_3)_2CF(CH_2)_nI]$, was analyzed using $^1$H-NMR. $^1$H-NMR resonances observed at 1.2 to 2.0 parts per million (ppm) were ascribed to $(CF_3)_2CFCH_2(CH_2)_{n-2}$—, and those observed at 3.2 ppm were ascribed to a terminal —$CH_2I$. The areas under these resonances were measured. The addition of 1 (to account for the $CH_2$ moiety contained in the terminal —$CH_2I$ group) to the ratio of the area for the resonances at 1.2 to 2.0 ppm to that of the resonance at 3.2 ppm gave an estimated number average value of n for the formula $[(CF_3)_2CF(CH_2)_nI]$ of 15.5 for the product of Example 1.

Examples 2-6

Telomerization of Ethylene Using Various Different Telogens

Examples 2-6 were carried out in essentially the same manner as that described above for Example 1, except that the type and the amount of the reactants were varied as summarized in Table 1 below.

TABLE 1

| Example No. | Telogen, Weight of Telogen (g) | Weight of Ethylene (g) | Ethylene: Telogen Molar Ratio | Wt. of t-Butyl Benzoylperoxide (g) |
|---|---|---|---|---|
| 2 | $(CF_3)_2CFCH_2CH_2I$, 3.4 | 15.0 | 50.8 | 0.08 (AIBN) |
| 3 | $CF_3CF_2CH_2I$, 8.1 | 15.2 | 17.5 | 0.214 |
| 4 | $CF_3(CF_2)_3SO_2N(Me)CH_2CH_2I$, 2.0 | 16.7 | 139.3 | 0.074 |
| 5 | $FO_2S(CF_2)_2O(CF_2)_2I$, 2.0 | 18.3 | 134.0 | 0.0734 |
| 6 | $C_3F_6O(i$-$C_3F_6O)_5CF$—$(CF_3)I$, $M_n = 1200$, 2.0 | 16.2 | 346.6 | 0.0704 |

Estimated number average values of n for the product telomer mixtures of formula $[R(CH_2)_nX]$ were determined for each of Examples 2-6 and are reported in Table 2 below. (where R and X correspond to the R and X of a particular telogen, RX, that was used for the particular Example). The estimated number average values of n reported in Table 2 were determined and calculated using the $^1$H-NMR technique described above for Example 1.

TABLE 2

| Example No. | Number Average Value of n for $R(CH_2)_nX$ Telomer Distribution |
|---|---|
| 2 | 28.8 |
| 3 | 12.2 |
| 4 | 27.4 |

TABLE 2-continued

| Example No. | Number Average Value of n for $R(CH_2)_nX$ Telomer Distribution |
|---|---|
| 5 | 57.4 |
| 6 | 19.5 |

Example 7

Telomerization of Ethylene Using a Telogen Mixture (Prepared by Telomerization of Ethylene Using Perfluorobutyl Iodide)

A 183 mL stainless steel autoclave was charged with 17.2 g of $C_4F_9I$ and 0.457 g of t-butyl perbenzoate. After the autoclave was cooled in a dry ice bath and degassed using a vacuum pump, 14.4 g of ethylene was added. The autoclave was shaken and heated to 100° C. and held at 100° C. overnight. The autoclave was then cooled to room temperature, any remaining gases were released, and 26.0 g of wax-like product was recovered. The product was analyzed by $^1$H-NMR to be $C_4F_9(CH_2)_{16.6}I$.

10.0 g of the product was placed in the 183 mL stainless steel autoclave, along with 0.270 g t-butyl perbenzoate and 66.2 g ethylene. The above-described process was repeated. After holding at 100° C. overnight, the autoclave was cooled to room temperature, any remaining gases were released, and 12.8 g of product was recovered. The number average value of n for the product was determined by $^1$H-NMR to be 23.4.

Example 8

Conversion of a Telomer Distribution to the Corresponding Alcohols, $C_4F_9(CH_2)_{17.6}OH$ A mixture of 8.1 g of $C_4F_9(CH_2)_{17.6}I$ (number average n value=17.6), 8.1 g sodium acetate, and 80 mL DMSO was stirred and heated to 135° C. After 18 hours at 135° C., the resulting mixture was poured into water. The resulting solid was collected and re-dissolved in THF. The THF solution was filtered to remove residual salts and then was concentrated to 7 g of a wax-like product. GC and $^1$H-NMR confirmed complete conversion to $C_4F_9(CH_2)_{17.6}OC(O)CH_3$. A mixture of 7 g of this ester, 0.19 g p-toluenesulfonic acid, and 500 mL ethanol was charged to a flask and heated at reflux for 48 hours. NaHCO$_3$ (0.19 g) was added to the flask, and the resulting solid was removed by filtration. After solvent was removed, 6.5 g of a wax-like product remained. GC and $^1$H-NMR confirmed complete conversion to C$_4$F$_9$(CH$_2$)$_{17.6}$OH.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A process comprising combining in a batchwise, semi-continuous, or continuous manner, or a combination thereof, in the presence of at least one free radical initiator, and at a temperature sufficient to cause said initiator to fragment to form free radicals, (a) at least one telogen selected from (1) fluoroalkyl halides that comprise at least one halomethylene moiety (—CHX—) and, optionally, at least one non-fluorine heteroatom, and (2) perfluoroalkyl halides that comprise at least one halofluoromethylene moiety (—CFX—) and at least one non-halogen heteroatom, said halides being selected from iodides and bromides; and (b) ethylene; said telogen and said ethylene being combined in total amounts such that the number of moles of ethylene per mole of telogen is at least 4.

2. The process of claim 1, wherein said telogen is selected from said fluoroalkyl halides and mixtures thereof.

3. The process of claim 1, wherein said halide is iodide.

4. The process of claim 1, wherein said halide is bromide.

5. The process of claim 1, wherein said telogen is saturated.

6. The process of claim 1, wherein said heteroatoms are selected from iodine, bromine, nitrogen, oxygen, sulfur, and mixtures thereof.

7. The process of claim 1, wherein said number of moles of ethylene per mole of telogen is at least 8.

8. The process of claim 1, wherein said number of moles of ethylene per mole of telogen is at least 10.

9. The process of claim 1, wherein said number of moles of ethylene per mole of telogen is at least 2 times the average number of moles of ethylene taxomons incorporated in the resulting telomer product, as calculated from the number average molecular weight of the product.

10. The process of claim 1, wherein said telogen is selected from the class of fluoroalkyl halides that is represented by the following general formula:

R'CH(R)X    (I)

wherein R' is fluorine or a fluoroalkyl or perfluoroalkyl group of 1 to 25 carbon atoms that optionally comprises at least one non-fluorine heteroatom and/or at least one alicyclic moiety; R is hydrogen, fluorine, or a fluoroalkyl or perfluoroalkyl group of 1 to 25 carbon atoms that optionally comprises at least one non-fluorine heteroatom and/or at least one alicyclic moiety; and X is iodine or bromine; with the proviso that optionally R' and R are bonded together to form an alicyclic ring having from 5 to 7 ring carbon atoms.

11. The process of claim 10, wherein said telogen is selected from CF$_3$CH$_2$I, CF$_3$OCH(CF$_3$)I, CF$_3$CH(CF$_3$)Br, H(CF$_2$)$_6$CH$_2$I, CF$_3$C$_3$H$_6$I, C$_2$F$_5$C$_2$H$_4$I, CF$_3$CH$_2$Br, C$_2$F$_5$C$_2$H$_4$Br, (CF$_3$)$_2$CFCH$_2$I, C$_4$F$_9$C$_2$H$_4$I, C$_4$F$_9$C$_3$H$_6$I, C$_4$F$_9$C$_4$H$_8$Br, C$_6$F$_{13}$CH$_2$Br, CF$_3$OC$_2$H$_4$I, C$_4$F$_9$OCH$_2$Br, C$_3$F$_7$CH$_2$OC$_2$H$_4$I, C$_4$F$_9$SO$_2$N(CH$_3$)C$_2$H$_4$I, C$_2$F$_5$OC$_2$F$_4$C$_2$H$_4$I, CF$_3$OC$_2$F$_4$CH$_2$Br, (CF$_3$)$_2$CHOC$_2$H$_4$I, C$_2$F$_5$SO$_2$N(CH$_3$)CH$_2$C(O)CH$_2$I, (CF$_3$)$_2$NC$_2$F$_4$CH$_2$I, C$_3$F$_7$N(CF$_3$)CF$_2$C$_2$H$_4$Br, FSO$_2$C$_3$F$_6$C$_2$H$_4$I, (CF$_3$)$_2$NCH$_2$I, (CF$_3$)$_2$NCF$_2$CH$_2$I, CH$_3$OC(O)C$_4$F$_8$CH$_2$I, (CF$_3$)$_2$CHI, and mixtures thereof.

12. The process of claim 1, wherein said telogen is a telogen mixture that is prepared by the process of claim 1 and recycled for further telomerization.

13. The process of claim 1, wherein said telogen is selected from the class of perfluoroalkyl halides that is represented by the following general formula:

R'''CF(R'')X    (II)

wherein R''' is a perfluoroalkyl group of 1 to 25 carbon atoms that optionally comprises at least one alicyclic moiety and/or at least one non-fluorine halogen atom; R'' is fluorine or a perfluoroalkyl group of 1 to 25 carbon atoms; and X is iodine or bromine; with the proviso that at least one of R''' and R'' comprises at least one non-halogen heteroatom, and with the further proviso that R''' and R'' optionally are bonded together to form an alicyclic ring having from 5 to 7 ring carbon atoms.

14. The process of claim 13, wherein said telogen is selected from FSO$_2$C$_2$F$_4$OC$_2$F$_4$I, FSO$_2$C$_3$F$_6$Br, CF$_3$OC$_2$F$_4$I, CF$_3$OCF(CF$_3$)I, (CF$_3$)$_2$CFOC$_2$F$_4$I, C$_3$F$_7$O(i-C$_3$F$_6$O)$_p$CF(CF$_3$)I (where p is an integer of 0 to 7), C$_3$F$_7$O(n-C$_3$F$_6$O)$_p$CF(CF$_3$)I (where p is an integer of 0 to 7), C$_3$F$_7$O(i-C$_3$F$_6$O)$_p$CF(CF$_3$)Br (where p is an integer of 0 to 7), FOC(O)C$_5$F$_{10}$I, and mixtures thereof.

15. The process of claim 1, wherein said telogen comprises a sulfonamido moiety, a perfluoropolyether moiety, or a perfluoroalkyl moiety having fewer than 6 carbon atoms.

16. The process of claim 1, wherein said temperature is from 0° C. to 250° C.

17. The process of claim 1, wherein said process is carried out in an inert reaction environment.

18. The process of claim 1, wherein said free radical initiator is selected from azo compounds, peroxides, hydroperoxides, peracids, peresters, thermal redox initiators, and mixtures thereof.

19. The process of claim 1, wherein said process further comprises (a) combining at least one resulting polymethylene halide telomer with at least one metal carboxylate; and (b) subjecting the resulting polymethylene carboxylate to alkanolysis; wherein said combining and said subjecting are carried out under substantially anhydrous conditions.

20. A process comprising combining in a batchwise, semi-continuous, or continuous manner, or a combination thereof, in the presence of at least one free radical initiator selected from azo compounds, peroxides, peresters, and mixtures thereof, under substantially oxygen-free conditions, and at a temperature from 75° C. to 125° C., (a) at least one telogen selected from (1) the class of fluoroalkyl halides that is represented by the following general formula:

R'CH(R)X    (1)

wherein R' is a fluoroalkyl or perfluoroalkyl group of 1 to 25 carbon atoms that optionally comprises at least one non-fluorine heteroatom; R is hydrogen or a perfluoroalkyl group of 1 to 6 carbon atoms; and X is iodine or bromine; and (2) the class of perfluoroalkyl halides that is represented by the following general formula:

R'''CF(R'')X    (II)

wherein R''' is a perfluoroalkyl group of 1 to 25 carbon atoms that comprises at least one non-halogen heteroatom; R'' is fluorine or a perfluoroalkyl group of 1 to 6 carbon atoms; and X is iodine or bromine; and (b) ethylene; said telogen and said ethylene being combined in total amounts such that the number of moles of ethylene per mole of telogen is at least 8.

* * * * *

UNITED STATES PATENT AND TRADEMARK OFFICE
CERTIFICATE OF CORRECTION

PATENT NO. : 7,893,186 B2
APPLICATION NO. : 12/519649
DATED : February 22, 2011
INVENTOR(S) : Yu Yang et al.

Page 1 of 1

It is certified that error appears in the above-identified patent and that said Letters Patent is hereby corrected as shown below:

Title Page 2
Column 2 (Other Publications); Line 7, Delete "Iodoperiluoroalkanes" and insert
-- iodoperfluoralkanes --, therefor.

Column 10
Line 46; Delete "$C_3F_6O(isoC_3F_3O)_5CF(CF_3)$" and insert -- $C_3F_6O(isoC_3F_6O)_5CF(CF_3)I$ --, therefor.

Signed and Sealed this
Twenty-first Day of June, 2011

David J. Kappos
*Director of the United States Patent and Trademark Office*